US012657338B2

(12) United States Patent
Adame et al.

(10) Patent No.: US 12,657,338 B2
(45) Date of Patent: Jun. 16, 2026

(54) SYSTEMS AND METHODS TO MANAGE DATA SETS WHILE MAINTAINING DATA SET ISOLATION AND INTEGRITY

(71) Applicant: Express Scripts Strategic Development, Inc., St. Louis, MO (US)

(72) Inventors: Sherri C. Adame, Bloomfield, CT (US); Pranav Kapil, South Windsor, CT (US)

(73) Assignee: Express Scripts Strategic Development, Inc., St. Louis, MO (US)

( * ) Notice: Subject to any disclaimer, the term of this patent is extended or adjusted under 35 U.S.C. 154(b) by 137 days.

(21) Appl. No.: 18/736,775

(22) Filed: Jun. 7, 2024

(65) Prior Publication Data

US 2025/0378202 A1     Dec. 11, 2025

(51) Int. Cl.
*G06F 21/62* (2013.01)
*G16H 10/60* (2018.01)

(52) U.S. Cl.
CPC ......... *G06F 21/6245* (2013.01); *G16H 10/60* (2018.01)

(58) Field of Classification Search
None
See application file for complete search history.

(56) References Cited

U.S. PATENT DOCUMENTS

| | | | |
|---|---|---|---|
| 9,063,746 B2 | 6/2015 | Yousouf | |
| 10,169,533 B2 | 1/2019 | Hernandez | |
| 10,652,207 B2 | 5/2020 | Voss | |
| 2002/0071564 A1 | 6/2002 | Kurn | |
| 2003/0115082 A1 | 6/2003 | Jacobson | |
| 2005/0049882 A1 | 3/2005 | Sawka | |
| 2005/0071195 A1 | 3/2005 | Cassel | |
| 2005/0071842 A1 | 3/2005 | Shastry | |
| 2005/0246205 A1* | 11/2005 | Wang ..................... | G16H 10/60 705/3 |
| 2006/0287890 A1* | 12/2006 | Stead ..................... | G16H 10/20 705/3 |
| 2012/0035961 A1 | 2/2012 | Dvorak | |
| 2016/0117448 A1* | 4/2016 | Van De Craen ....... | G16H 10/60 705/3 |

* cited by examiner

*Primary Examiner* — Boris D Grijalva Lobos

(57) ABSTRACT

A method for managing Master Data Management (MDM) data sets is provided. The method stores a second MDM data set into a second data repository separate and distinct from a first data repository storing a first MDM data set; continuously protects data integrity of the first and second MDM data sets, by: (i) maintaining separation between the first data repository and the second data repository, and (ii) preventing unauthorized data sharing by the first and second MDM data sets; detects a change to an MDM record of the first MDM data set, via a communication platform; determines that the second MDM data set includes a second MDM record associated with the patient, based on recognition of the patient by the second data repository; creates a cross-reference identifier for the patient; and updates the first MDM data set and the second MDM data set to include the cross-reference identifier.

19 Claims, 8 Drawing Sheets

SYSTEMS AND METHODS TO MANAGE DATA SETS WHILE MAINTAINING DATA SET ISOLATION AND INTEGRITY

TECHNICAL FIELD

Embodiments of the subject matter described herein relate generally to using one or more Master Data Management (MDM) protocols. More particularly, embodiments of the subject matter relate to using MDM data sets or other data objects in an enterprise computing environment.

BACKGROUND

In an enterprise computing environment, data management may be a complex and/or cumbersome task, due to a potentially large quantity of data assets. Multiple data assets may need to be stored, maintained, and used for separate and particular purposes. For example, an enterprise computing environment may be associated with various departments, divisions, subsidiaries, or other distinct entities. Business mergers and acquisitions may also be associated with new data assets associated with distinct entities. Commonalities may exist between distinct data assets, but how to approach such commonalities may be difficult due to concerns including ensuring data security, data integrity, compliance with regulations, or the like.

BRIEF SUMMARY

Systems and methods are provided for managing data sets (e.g., Master Data Management (MDM) data sets) in an enterprise computing environment, while maintaining data set isolation and integrity.

Some embodiments provided by the present disclosure include a system for managing Master Data Management (MDM) data sets in an enterprise computing environment. The system includes: a first data repository comprising at least a first processing element, a memory element, and a first communication element, wherein the first data repository is configured to store and maintain a first Master Data Management (MDM) data set; a communication platform comprising a broadcast communication medium connecting a primary computing system to at least the first data repository in the enterprise computing environment; and the primary computing system comprising at least one processor and a system memory element, wherein the primary computing system is communicatively coupled to the first data repository using the communication platform.

The primary computing system is configured to: acquire a second Master Data Management (MDM) data set into the enterprise computing environment; store the second MDM data set into a second data repository separate and distinct from the first data repository; and continuously protect data integrity of the first MDM data set and the second MDM data set, by: (i) maintaining separation between the first data repository and the second data repository, and (ii) preventing unauthorized data sharing by the first MDM data set and the second MDM data set. The primary computing system is further configured to: detect a change to an MDM record of the first MDM data set, via the communication platform connected to the enterprise computing environment including at least the primary computing system, the first data repository, and the second data repository, wherein the MDM record is associated with a patient; determine that the second MDM data set includes a second MDM record associated with the patient, based on recognition of the patient by the second data repository; create a cross-reference identifier for the patient; and update the first MDM data set and the second MDM data set to include the cross-reference identifier, via the communication platform.

Some embodiments provided by the present disclosure include a method for using Master Data Management (MDM) data sets in an enterprise computing environment. The method acquires a second Master Data Management (MDM) data set into the enterprise computing environment, by a primary computing system communicatively coupled to a first data repository storing a first MDM data set; stores the second MDM data set into a second data repository separate and distinct from the first data repository, by the primary computing system; and continuously protects data integrity of the first MDM data set and the second MDM data set, by the primary computing system, by: (i) maintaining separation between the first data repository and the second data repository, and (ii) preventing unauthorized data sharing by the first MDM data set and the second MDM data set.

The method further detects a change to an MDM record of the first MDM data set, by the primary computing system via a communication platform connected to the enterprise computing environment including at least the primary computing system, the first data repository, and the second data repository, wherein the MDM record is associated with a patient; determines that the second MDM data set includes a second MDM record associated with the patient, by the primary computing system, based on recognition of the patient by the second data repository; creates a cross-reference identifier for the patient, by the primary computing system; and updates the first MDM data set and the second MDM data set to include the cross-reference identifier, by the primary computing system.

This summary is provided to introduce a selection of concepts in a simplified form that are further described below in the detailed description. This summary is not intended to identify key features or essential features of the claimed subject matter, nor is it intended to be used as an aid in determining the scope of the claimed subject matter.

BRIEF DESCRIPTION OF THE DRAWINGS

A more complete understanding of the subject matter may be derived by referring to the detailed description and claims when considered in conjunction with the following figures, wherein like reference numbers refer to similar elements throughout the figures.

DETAILED DESCRIPTION

Figure 1:
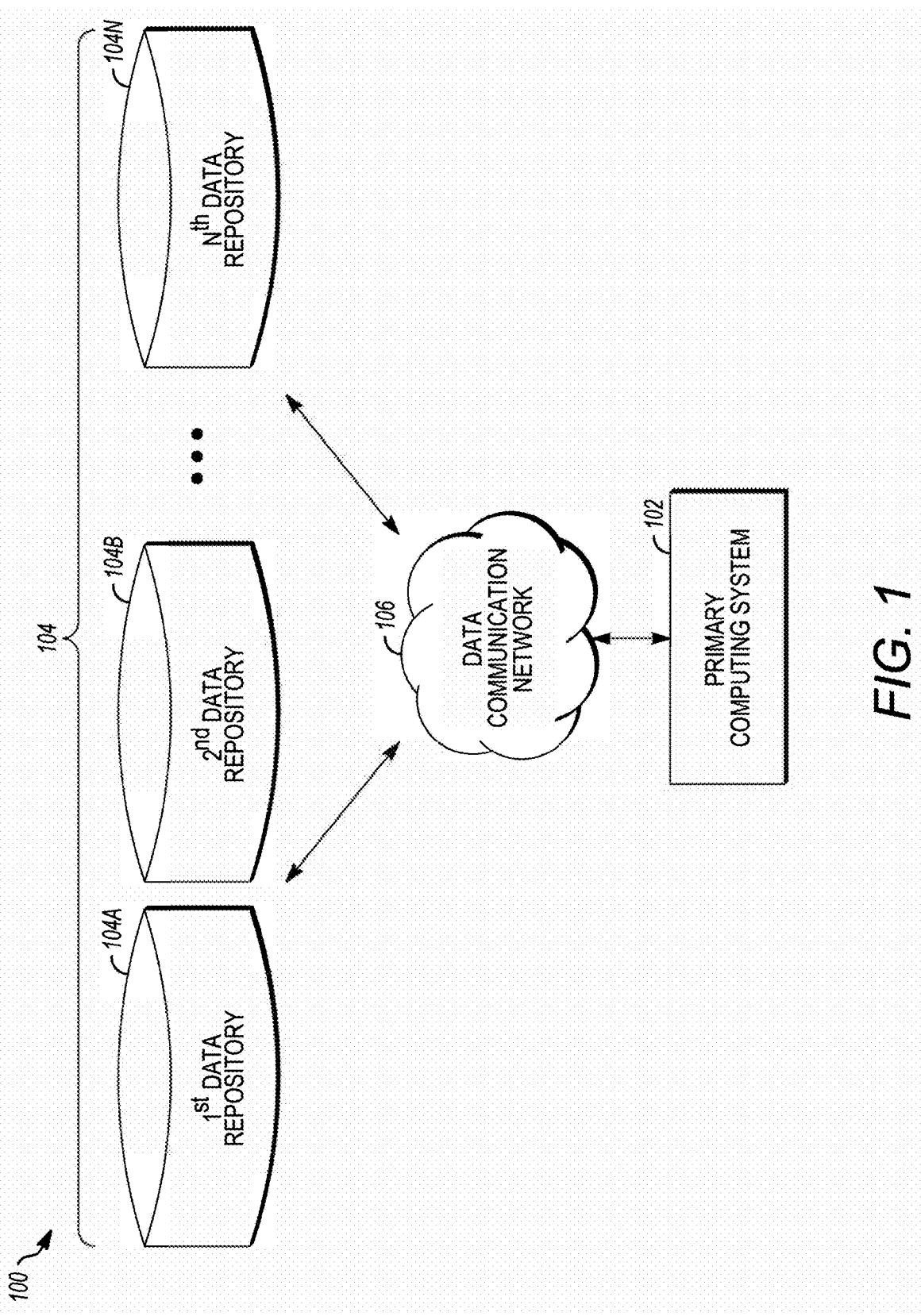
FIG. 1 is a diagram of a system for implementing a framework for managing data sets, in accordance with the disclosed embodiments.

The following detailed description is merely illustrative in nature and is not intended to limit the embodiments of the subject matter or the application and uses of such embodiments. As used herein, the word "exemplary" means "serving as an example, instance, or illustration." Any implementation described herein as exemplary is not necessarily to be construed as preferred or advantageous over other implementations. Furthermore, there is no intention to be bound by any expressed or implied theory presented in the preceding technical field, background, brief summary or the following detailed description.

The subject matter presented herein relates to systems and methods for managing a plurality of disparate Master Data Management (MDM) data sets while maintaining separation of the data sets. More specifically, the subject matter relates to managing MDM data sets at a high level, wherein patients may be identified at the enterprise level such that MDM data for the patient from any isolated MDM may be recognized, obtained, and/or used at the enterprise level. Systems implementing these high-level operations maintain data integrity of each MDM data set, since each MDM data set remains unchanged by the enterprise-level processes performed outside of the MDM data sets and/or MDM data repositories.

Certain terminologies are used with regard to the various embodiments of the present disclosure.

Master Data Management (MDM) may refer to any techniques or procedures for maintaining data assets for an enterprise computing environment, according to policies set by the enterprise. An MDM data set may include a collection of data associated with a particular MDM, wherein the MDM data set is maintained as a separate entity that is distinct from other MDM data sets in an enterprise computing environment.

A primary computing system, within the context of this disclosure, is any computing system operable to communicate with a plurality of data repositories configured to store and maintain Master Data Management (MDM) data sets, for purposes of implementing a framework that creates and uses Master Individual Identifiers (MIIs) for patients associated with records included in the MDM data sets. The primary computing system may be implemented using a computing device or system that includes at least one processor, system memory, and some form of input and output (I/O) communication hardware (e.g., a communication device to implement various protocols, communication ports for wired connections, wireless communication capabilities).

A data repository may include any computer memory hardware operable to store and maintain at least MDM data, MDM data sets, and/or executable instructions or logical rules for MDM data management. As described herein, a data repository includes, or is communicatively coupled to, at least one processor, memory, and any applicable form of input and output (I/O) communication hardware (e.g., a communication device to implement various protocols, communication ports for wired connections, wireless communication capabilities). As such, embodiments of a data repository may include any type and any number of computing devices or servers.

A communication platform may include any type of network communication structures and/or components operable to connect parts of the MDM data management system for broadcast data communications. The communication platform broadcasts data transmissions such that all data transmissions are received by all connected parts of the MDM data management system, wherein each of the connected parts is operable to determine whether a data transmission is applicable to itself and to initiate procedures and processes in response to an applicable data transmission.

Turning now to the figures, FIG. 1 is a diagram of a system 100 for implementing a framework for managing data sets, in accordance with the disclosed embodiments. As shown, the system 100 includes a primary computing system 102 in communication with a plurality of data repositories 104. In practice, an embodiment of the system 100 may include additional or alternative elements and components, as desired for the particular application. For example, additional components such as displays and user input components may be employed without departing from the scope of the present disclosure.

A primary computing system, within the context of this disclosure, is any computing system operable to communicate with a plurality of data repositories configured to store and maintain Master Data Management (MDM) data sets, for purposes of implementing a framework that creates and uses Master Individual Identifiers (MIIs) for patients associated with records included in the MDM data sets. The primary computing system may be implemented using a computing device or system that includes at least one processor, system memory, and some form of input and output (I/O) communication hardware (e.g., a communication device to implement various protocols, communication ports for wired connections, wireless communication capabilities).

A data repository may include any computer memory hardware operable to store and maintain at least MDM data, MDM data sets, and/or executable instructions or logical rules for MDM data management. As described herein, a data repository includes, or is communicatively coupled to, at least one processor and any applicable form of input and output (I/O) communication hardware (e.g., a communication device to implement various protocols, communication ports for wired connections, wireless communication capabilities). As such, embodiments of a data repository may include any type and any number of computing devices or servers.

The data communication network 106 may be any digital or other communications network capable of transmitting messages or data between devices, systems, or components. In certain embodiments, the data communication network 106 includes a packet switched network that facilitates packet-based data communication, addressing, and data routing. The packet switched network could be, for example, a wide area network, the Internet, or the like. In various embodiments, the data communication network 106 includes any number of public or private data connections, links, or network connections supporting any number of communications protocols. In various embodiments, the data communication network 106 could also incorporate a wireless and/or wired telephone network, such as a cellular communications network for communicating with mobile phones, personal digital assistants, or the like. The data communication network 106 may also incorporate any sort of wireless or wired local and/or personal area networks, such as one or more IEEE 802.3, IEEE 802.16, and/or IEEE 802.11 networks, and/or networks that implement a short range (e.g., Bluetooth) protocol. For the sake of brevity, conventional techniques related to data transmission, signaling, network control, and other functional aspects of the systems (and the individual operating components of the systems) may not be described in detail herein.

For communications between the primary computing system 102 and the data repositories 104, or communications between the data repositories 104 (e.g., a first data repository 104A communicating with a second data repository 104B), the system 100 implements a communication platform comprising a broadcast communication medium that connects the primary computing system 102 and applicable data repositories 104 in the enterprise computing environment. In some embodiments, the primary computing system 102 is connected to at least a first data repository 104A and a second data repository 104B via the communication platform. In some embodiments, the primary computing system 102 is connected to an n-number of data repositories, wherein n is greater than two. Example embodiments of the communication platform may include Kafka or other platforms capable of providing broadcast communications connections in the enterprise computing environment. Suitable alternatives may include synchronous embodiments (e.g., Application Programming Interface (API) calls) and/or asynchronous embodiments (e.g., message queues).

In practice, the primary computing system 102 implements a framework for creating, storing, and maintaining a Master Individual Identifier (MII) for a particular patient associated with patient records included in more than one MDM. The system 100 maintains each MDM as a separate and distinct entity that is stored in a separate and distinct data repository 104. Such a separation may be upheld for purposes of data integrity, compliance, or the like. The MII may be used in the enterprise computing environment as a high-level identification and association between records for the particular patient, when a first subset of the records in a first MDM is isolated from a second subset of the records in a second MDM. Thus, the system 100 can use a "consolidated" identifier for a patient that refers to a complete set of records for the patient, without combining or merging the MDMs such that the required separation is maintained.

Figure 2:
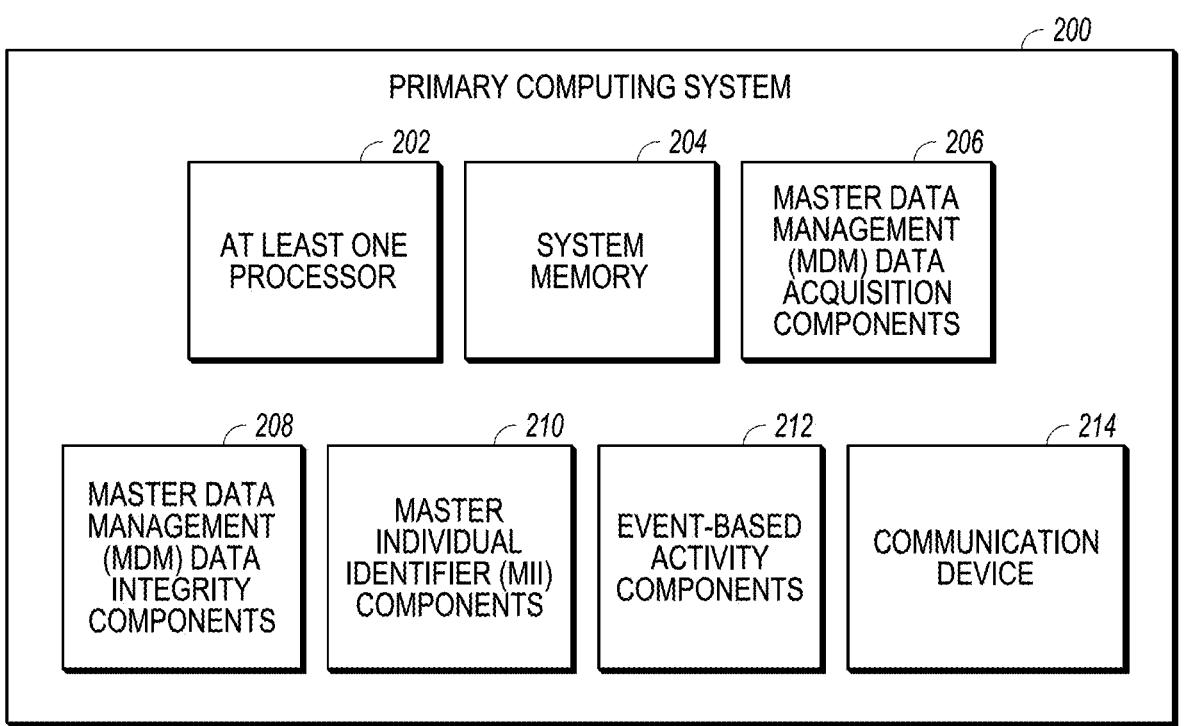
FIG. 2 is a functional block diagram of a primary computing system, in accordance with the disclosed embodiments.

FIG. 2 is a functional block diagram of a primary computing system 200, in accordance with the disclosed embodiments. It should be noted that the primary computing system 200 can be implemented with the primary computing system 102 depicted in FIG. 1. In this regard, the primary computing system 200 shows certain elements and components of the primary computing system 102 in more detail.

The primary computing system 200 may include, without limitation: at least one processor 202; a system memory 204 element; Master Data Management (MDM) data acquisition components 206; MDM data integrity components 208; Master Individual Identifier (MII) components 210; event-based activity components 212; and a communication device 214. These elements and features of the primary computing system 200 may be operatively associated with one another, coupled to one another, or otherwise configured to cooperate with one another as needed to support the desired functionality-in particular, implementing a framework to perform MDM data set management operations, as described herein. For ease of illustration and clarity, the various physical, electrical, and logical couplings and interconnections for these elements and features are not depicted in FIG. 2. Moreover, it should be appreciated that embodiments of the primary computing system 200 will include other elements, modules, and features that cooperate to support the desired functionality. For simplicity, FIG. 2 only depicts certain elements that relate to the MDM data set management techniques described in more detail below.

The at least one processor 202 may be implemented or performed with one or more general purpose processors or processor circuitry, a content addressable memory, a digital signal processor, an application specific integrated circuit, a field programmable gate array, any suitable programmable logic device, discrete gate or transistor logic, discrete hardware components, or any combination designed to perform the functions described here. In particular, the at least one processor 202 may be realized as one or more microprocessors, controllers, microcontrollers, or state machines. Moreover, the at least one processor 202 may be implemented as a combination of computing devices, e.g., a combination of digital signal processors and microprocessors, a plurality of microprocessors, one or more microprocessors in conjunction with a digital signal processor core, or any other such configuration.

The at least one processor 202 is communicatively coupled to the system memory 204 element. The system memory 204 is configured to store any obtained or generated data associated with performing MDM data management operations by the primary computing system 200. The system memory 204 may be realized using any number of devices, components, or modules, as appropriate to the embodiment. Moreover, the primary computing system 200 could include a system memory 204 element integrated therein and/or a system memory 204 element operatively coupled thereto, as appropriate to the particular embodiment. In practice, the system memory 204 could be realized as RAM memory, flash memory, EPROM memory, EEPROM memory, registers, a hard disk, a removable disk, or any other form of storage medium known in the art. In certain embodiments, the system memory 204 includes a hard disk, which may also be used to support functions of the primary computing system 200. The system memory 204 can be coupled to the at least one processor 202 such that the at least one processor 202 can read information from, and write information to, the system memory 204. In the alternative, the system memory 204 may be integral to the at least one processor 202. As an example, the at least one processor 202 and the system memory 204 may reside in a suitably designed application-specific integrated circuit (ASIC).

The Master Data Management (MDM) data acquisition components 206 are operable to integrate one or more separate and distinct MDM data sets into an enterprise computing environment. For example, an enterprise computing environment may include computing assets associated with a particular enterprise. In other words, an enterprise may own, lease, use, or otherwise control a set of computing assets. Such computing assets may include hardware and software components. In an enterprise computing environment, computing assets may be networked or non-networked, depending on the particular asset and the use of the asset by the enterprise. MDM data acquisition components 206 may incorporate an MDM data set into a connected environment, wherein a new MDM data set may be saved in a data repository or other memory components that are communicatively coupled to the primary computing system 200.

MDM data integrity components 208 are operable to maintain separation of each MDM such that the integrity of each set of MDM data is preserved. To accomplish this, the MDM data integrity components 208 permit the MDMs to publish only an identifier for a patient associated with a patient record. The MDMs are not permitted to publish any other data associated with a patient. Data integrity is a critical priority for each MDM, as each MDM may be used for a different purpose, and/or may be owned by different companies or subsidiaries of a particular company. Maintaining intact and unchanged MDM data is possible when an MDM data set is not merged with other MDM data sets or, in other words, when MDMs are not combined or integrated together.

Master Individual Identifier (MII) components 210 are operable to create, store, maintain, and update an MII for each patient having records stored in a plurality of MDMs. The MII is a high-level patient identifier that is unrelated to other data or identifiers used by the MDMs. The MII is a created identifier that is unique for each patient, and therefore, an MII refers to only one patient and is not shared between patients.

The event-based activity components 212 are operable to detect relevant broadcast events, and to initiate or "trigger" operations of the primary computing system 200 in response to specific operations occurring in the enterprise computing environment. Exemplary embodiments of relevant broadcast events include data transmissions indicating a recent change to one or more MDM records. However, it should be appreciated that other embodiments may include additional and/or alternative types of relevant broadcast events.

The communication device 214 is suitably configured to communicate data between the primary computing system 200 and a plurality of data repositories (see reference 104, FIG. 1), wherein each data repository is operable to store and maintain an MDM. Certain embodiments of the communication device 214 may also be configured to transmit and receive communications between the primary computing system 200 and other external computing devices (e.g., a personal computing device, a server, external computer storage, or the like). The communication device 214 may transmit and receive communications over a wireless local area network (WLAN), the Internet, a satellite uplink/downlink, a cellular network, a broadband network, a wide area network, or the like. As described in more detail herein, data received by the communication device 214 may include, without limitation: broadcast data transmissions from one or more MDMs, and other data compatible with the primary computing device 200. Data provided by the communication device 214 may include, without limitation: requests for one or more MDMs to search for a particular patient, data transmissions to store a Master Individual Identifier (MII) in a local database, and the like.

In practice, the MDM data acquisition components 206, MDM data integrity components 208, MII components 210, and/or event-based activity components 212 may be implemented with (or cooperate with) the at least one processor 202 to perform at least some of the functions and operations described in more detail herein. In this regard, the MDM data acquisition components 206, MDM data integrity components 208, MII components 210, and/or event-based activity components 212 may be realized as suitably written processing logic, application program code, or the like.

Figure 3:
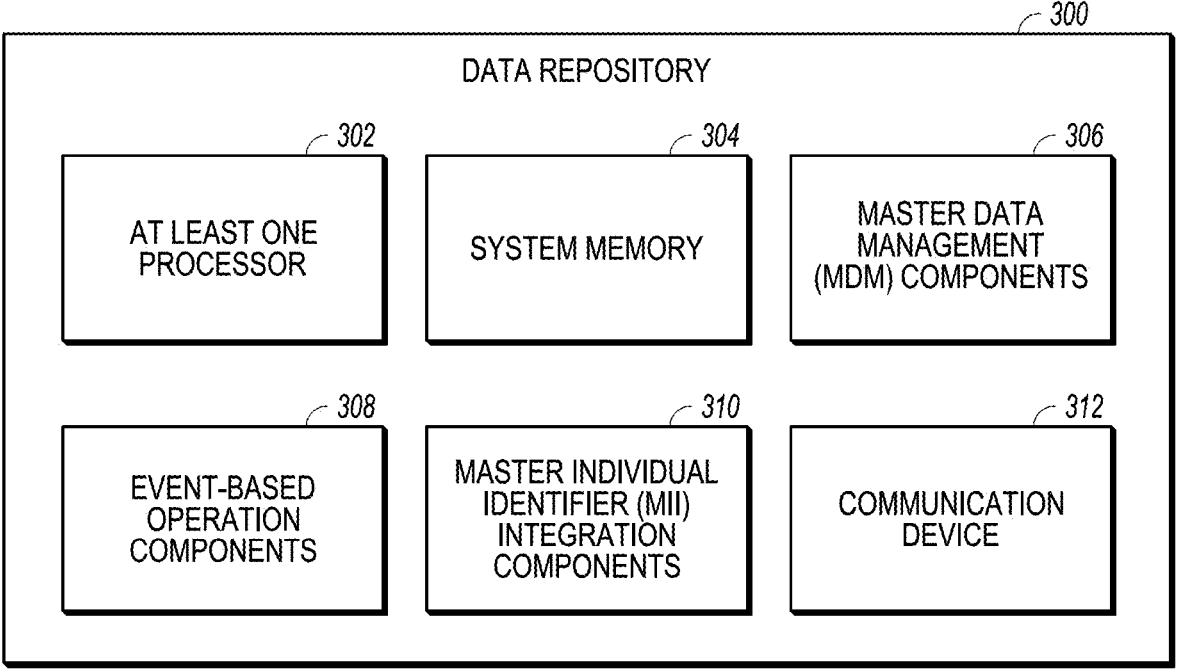
FIG. 3 is a functional block diagram of a data repository for use in the system for managing data sets, in accordance with the disclosed embodiments.

FIG. 3 is a functional block diagram of a data repository for use in the system (see reference 100, FIG. 1) for managing data sets, in accordance with the disclosed embodiments. It should be noted that the data repository 300 can be implemented with one of the data repositories 104 depicted in FIG. 1. In this regard, the data repository 300 shows certain elements and components of the data repositories 104 in more detail.

The data repository 300 may include, without limitation: at least one processor 302; a system memory 304 element; Master Data Management (MDM) components 306; event-based operation components 308; Master Individual Identifier (MII) integration components 310; and a communication device 312. It should be noted that the at least one processor 302, the system memory 304, and the communication device 312 were described previously with regard to references 202, 204, and 214 of FIG. 2, and will not be redundantly described here.

The Master Data Management (MDM) components 306 are suitably configured to perform MDM operations for a particular MDM data set associated with the data repository 300, wherein the MDM data set is separate and distinct from other MDM data sets associated with the enterprise or system (e.g., reference 100 of FIG. 1). For example, an MDM data set may be stored in the system memory 304, and the MDM components 306 are operable to perform internal data manipulation according to rules and/or procedures specific to the MDM data set.

The event-based operation components 308 are operable to receive communications broadcast via a communication platform. In this way, the event-based operation components 308 recognize communications directed to the data repository 300, and performs appropriate operations based on an event, wherein the event is the occurrence of receiving the communication. The event-based operation components 308 disregard communications that are not directed to the data repository 300. In some embodiments, the event-based operation components 308 may perform internal data manipulation operations based on an event. In some embodiments, the event-based operation components 308 may perform operations related to creating and/or recognizing a Master Individual Identifier (MII) based on an event, as described herein.

The Master Individual Identifier (MII) integration components 310 are operable to obtain an MII for a patient that the data repository 300 has acknowledged (via broadcast message) exists in the MDM data set associated with the data repository 300. When the MII is obtained for a currently existing patient record, the MII integration components 310 associated the new MII with the patient record and incorporate the MII into the MDM data set. However, when the data repository 300 has not acknowledged that the patient exists in the MDM data set, indicating that the patient is not associated with current records of the MDM data set, then the MII integration components 310 do not obtain an MII. In this scenario, a patient record to associate with an MII is not included in the MDM data set and therefore an MII is not used.

Figure 4:
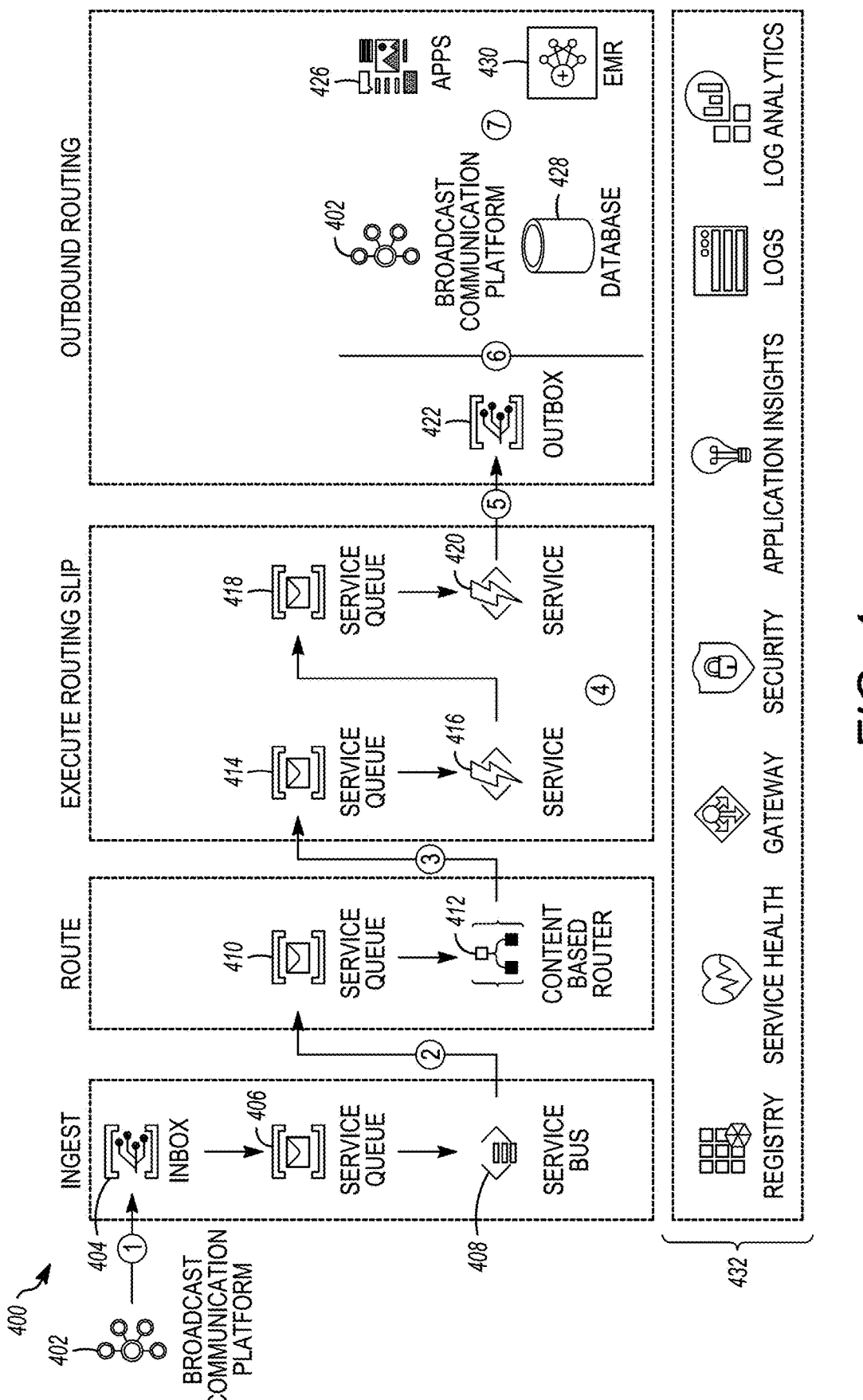
FIG. 4 is a diagram of an embodiment of a framework 400 for managing data sets in an enterprise computing environment, in accordance with the disclosed embodiments.

FIG. 4 is a diagram of an embodiment of a framework 400 for managing data sets in an enterprise computing environment, in accordance with the disclosed embodiments. The framework 400 may be implemented using a primary computing system (e.g., FIG. 1, reference 102; FIG. 2, reference 200). It should be appreciated that FIG. 4 depicts a simplified embodiment of the framework 400, and that some implementations of the framework 400 may include additional elements or components.

As shown, the framework 400 includes a broadcast communication platform 402 that broadcasts data messages transmitted by any of a plurality of MDMs and/or the framework 400 itself. Embodiments of the broadcast communication platform 402 may include Kafka or other platforms capable of providing broadcast communications connections in the enterprise computing environment. Suitable alternatives may include synchronous embodiments (e.g., Application Programming Interface (API) calls) and/or asynchronous embodiments (e.g., message queues). Data messages communicated via the broadcast communication platform 402 are received by the framework 400 via an inbox 404 or other data input component or mechanism. Thus, the inbox 404 is operable to obtain data messages and move data messages into an implementation of the framework 400.

From the inbox 404, an input data message enters a service queue 406 for a service bus 408. The input data message is moved to the service bus 408 according to positioning in the service queue 406. The input data message then transitions out of the data input stage, for processing.

The input data message transitions from the data input stage into the data routing stage of the procedure by moving into a second service queue 410 for a content-based router 412. The input data message is evaluated by the content-based router 412 according to positioning in the service queue 410. The content-based router 412 evaluates the content of the input data message and determines applicable processing for the input data message, or in other words, to which services the input data message will be routed for appropriate processing. Once the appropriate processing is determined, the content-based router 412 attaches a routing slip to the input data message, wherein the routing slip (i) identifies the services applicable to processing the data input message, and (ii) provides a sequence for executing each of the services. Embodiments of a routing slip may include an ordered list of service indicators for routing the data input message.

To determine appropriate processing for the data input message, the content-based router 412 performs a lookup in a database of predetermined workflows. Each predetermined workflow is associated with at least one particular use-case, and each particular use-case is associated with at least one conditional statement (i.e., an "if-then" statement). The content-based router 412 identifies a workflow that aligns with the content of the input data message, determines the services 416, 420 required to execute the workflow, and determines the sequence of the services 416, 420 required to execute the workflow. The content-based router 412 attaches a routing slip to the input data message based on the determined services 416, 420 and the determined sequence of the services 416, 420. In the particular example shown, the services 416, 420 are aligned with a predetermined workflow applicable to the input data message. However, it should be appreciated that any number of services may be applicable to a different input data message, based on any predetermined workflow applicable to the different input data message, as determined by the content-based router 412.

In some embodiments, a routing slip may be stored in the database and associated with one or more corresponding workflows. In this scenario, the content-based router 412 is capable of obtaining the routing slip from the database. In some embodiments, a routing slip may be determined and constructed in real-time, upon determination of the applicable workflow for processing the data input message. Alternatively, a routing slip may be obtained from any alternative data storage accessible to the content-based router 412.

Once the routing slip is attached to the input data message, a combination data message, including the input data message and the appended routing slip, is ready for processing. In other words, the framework 400 is operable to execute the routing slip, or to execute the workflow steps identified by the routing slip. From the content-based router 412, the combination data message is delegated or "routed" to the first service 416 for processing (via a third service queue 414), wherein the first service 416 is identified in the sequence of services 416, 420 included in the appended routing slip. Each of the services 416, 420 is capable of parsing the routing slip and determining the next service in sequence for delegating the input data message for processing. Here, the first service 416 determines that the second service 420 is the next service in the sequence identified in the routing slip, and the first service 416 delegates the combination data message to the second service 420 (via a fourth service queue 418). In embodiments including a third service, the second service 420 would determine the third service (not shown) as the next service in the sequence identified in the routing slip, and the second service 420 would delegate the combination data message to the third service.

Each service obtains the combination message, which includes the original input data message and the appended routing slip. Each service also obtains, or is capable of obtaining, the output results of previously executed services in the applicable workflow. For this purpose, the combination message and sets of output from services are serialized and stored in one or more database tables, and are available to the next service in the sequence of services included in the workflow.

When the routing slip has been executed, and thus the delegated services 416, 420 have completed operations, then the combination data message and the output from the last service in the sequence (e.g., the second service 420) is delegated to the outbox 422 as output of the framework 400. As shown, the outbox 422 may direct the output of the framework 400 to the broadcast communication platform 402, to any connected applications 426 (i.e., "apps"), to an Electronic Medical Records (EMR) system 430, to one or more databases 428 for storage, or to one or more remote servers (i.e., cloud storage).

The framework 400 also includes additional functions 432 to complement the data message routing and workflow execution functionality. Embodiments of the additional functions 432 may include counterpart features for use with the data message routing and workflow execution functionality described herein (e.g., operations to perform analysis of the routing and workflow services, executed steps, and/or generated output data). Some embodiments may include user-configurable options for the additional functions 432, such that a user may add or remove individual ones of the additional functions 432, on an as-needed basis. It should be appreciated that the additional functions 432 shown are exemplary in nature, and that any number of other functions or features may be included without departing from the scope of the present disclosure.

Exemplary embodiments of the additional functions 432 may include, but are not limited to: a service registry for tracking services 416, 420; a service health function for determining status of each of the services 416, 420; a gateway function for limiting access to the framework 400 to approved Application Programming Interfaces (APIs); a security function for providing preconfigured security operations applicable to the services 416, 420; an application insights function for obtaining and providing additional data regarding performance of particular applications; a logging function for recording and saving data associated with operation of the framework 400 and/or any of the services 416, 420; a log analytics function for providing charts, graphs, and/or other visual presentation of logged data.

Figure 5:
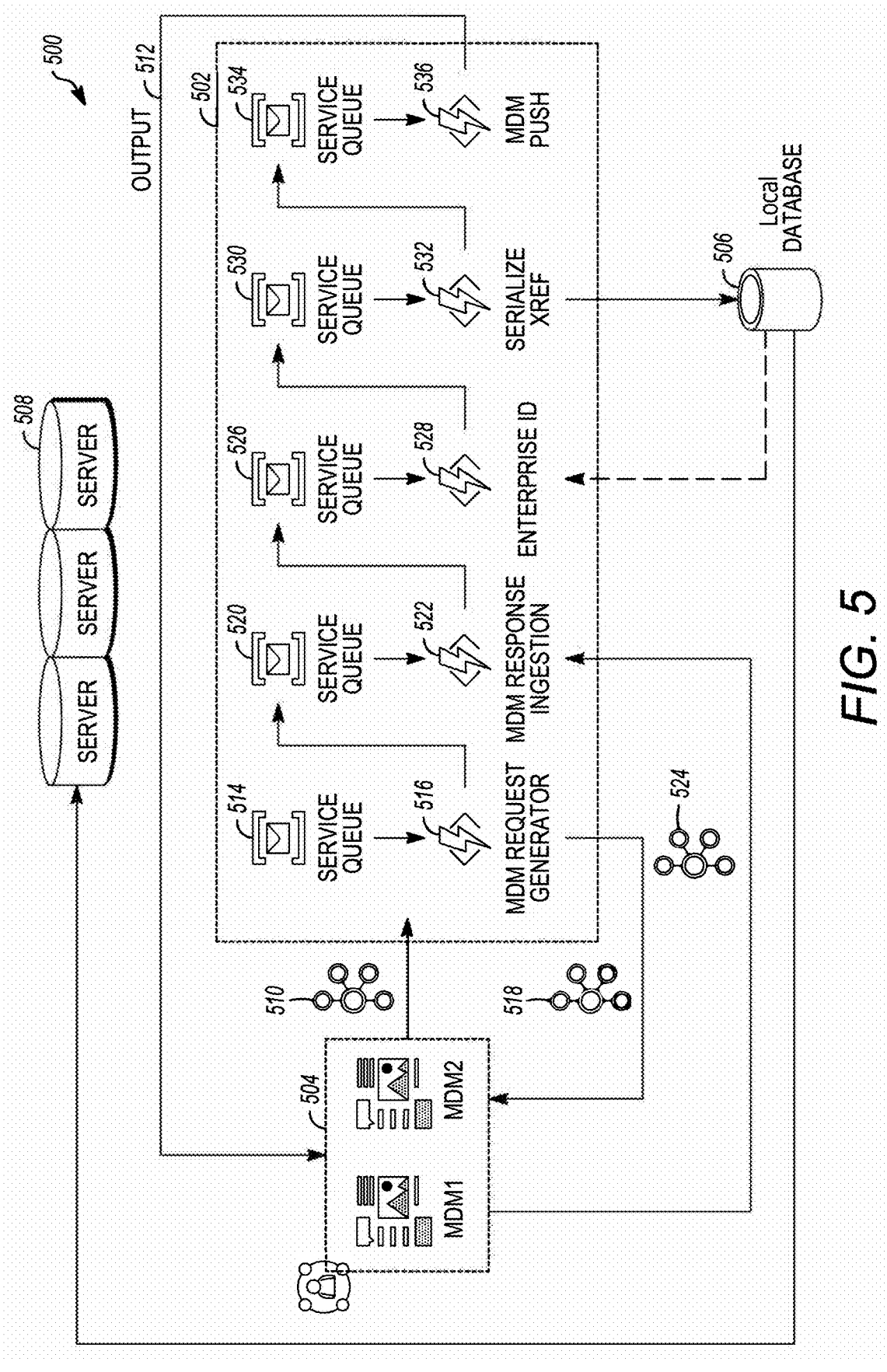
FIG. 5 is another diagram of an embodiment of a framework for managing data sets in an enterprise computing environment, in accordance with the disclosed embodiments.

The framework 400 may be implemented as part of a larger system. For example, FIG. 5 is another diagram of an embodiment of a framework 502 for managing data sets in an enterprise computing environment 500, in accordance with the disclosed embodiments. It should be appreciated that the enterprise computing environment 500 represents a "full featured" embodiment that supports various features described herein. In practice, an implementation of the enterprise computing environment 500 need not support all of the enhanced features described here and, therefore, one or more of the elements depicted in FIG. 5 may be omitted from other embodiments. Moreover, other implementations of the enterprise computing environment 500 may include additional elements and features that support conventional functions and operations.

As shown in FIG. 5, the enterprise computing environment 500 includes a plurality of Master Data Management (MDM) datasets 504 and a framework 502 for managing the MDM datasets 504. The MDM datasets 504 shown include "MDM 1" and "MDM 2". However, any number of datasets may be included as part of the enterprise computing environment 500, and any number of datasets may be managed by the framework 502. For purposes of the embodiment shown in FIG. 5, one of the MDM datasets 504 is a dataset that has been newly introduced into the enterprise computing environment 500, and the other one of the MDM datasets 504 is a previously existing dataset in the enterprise computing environment 500.

The framework 502 depicted in FIG. 5 is one particular embodiment of the framework described previously with regard to FIG. 4 (see reference 400). However, other embodiments of the framework of FIG. 4 may be implemented within the context of the present disclosure.

Here, the communication flow begins when a first one of the MDM datasets 504 detects a change to itself within the context of a record associated with a person. In this scenario, the change internal to the first one of the MDM datasets 504 triggers the event-driven architecture, and the first one of the MDM datasets 504 broadcasts a first data message 510 via a connected broadcast communication platform. The broadcast is received by the framework 502 and enters the service queue 514 for the first service, and MDM Request Generator 516. In response to receiving the data message indicating the change to a record in the first one of the MDM datasets 504, the MDM Request Generator 516 transmits a response data message 518 via the broadcast communication platform. The response data message includes a search request for a second one of the MDM datasets 504 to perform an internal search, within the contents of the second one of the MDM datasets 504, for the person associated with the change to a record in the first one of the MDM datasets 504. Here, the framework 502 is attempting to determine whether the person associated with a record in the first MDM is also associated with a record in the second MDM.

The second one of the MDM datasets 504 performs an internal search of the records of the second MDM dataset, for records associated with the person. For example, if the first one of the MDM datasets 504 updates a record associated with John Doe, then an event-triggered process begins whereby the first MDM dataset broadcasts the change to the record, and in response, the framework 502 broadcasts a search request to the second MDM dataset to search for any records associated with John Doe. If records associated with John Doe are included in both of the MDM datasets 504, then a Master Individual Identifier (MII) is needed for John Doe.

After performing an internal records search for the person, the second one of the MDM datasets 504 transmits, via the broadcast communication platform, a search response message 524 indicating whether or not the person is found in the second MDM dataset (i.e., whether any record in the second MDM dataset is associated with the particular person). The search response message 524 is received by the MDM Response Ingestion 522 service, and a combination of the input data message 510 with appended routing slip is transmitted to the service queue 520 for use by the MDM Response Ingestion 522 service when a response is received from the second MDM dataset.

When the search response message 524 indicates that the person is not associated with a record in the second MDM dataset, then the framework 502 takes no further action. In this scenario, an MII is not needed because the person is only associated with records in one of the MDM datasets 504. However, when the search response message 524 indicates that the person is associated with a record in the second MDM dataset, then the framework 502 continues as shown in FIG. 5. If the person is associated with records in both of the MDM datasets 504, then an MII is needed, in order to identify any records associated with the particular person in the enterprise computing system 500.

Here, the (i) combination of the input data message 510 with appended routing slip, and (ii) the output data from the MDM Response Ingestion 522 service, are delegated to the Enterprise ID 528 service via a service queue 520. The Enterprise ID 528 service communicates with a local database 506 to determine whether the particular person has a pre-existing MII. When the particular person has a pre-existing MII saved in the local database 506, then the framework 502 takes no further action. However, when the particular person has a pre-existing MII saved in the local database 506, then the Enterprise ID 528 service creates an MII and delegates the (i) combination of the input data message 510 with appended routing slip, and (ii) the output data from the Enterprise ID 528 service, to the Serialize XREF 532 service via a service queue 530. The Serialize XREF 532 service serializes the MII as a cross-reference between the MDM datasets 504, for the particular person, and saves the serialized cross-reference in the local database 506 and/or in one or more remote servers 508 for future use.

The Serialize XREF 532 service then delegates the (i) combination of the input data message 510 with appended routing slip, and (ii) the output data from the Serialize XREF 532 service, to the MDM push 536 service via a service queue 534. The MDM push 536 service then transmits, via the broadcast communication platform, an output data message 512 from the framework 502 to the MDM datasets 504. Here, the output data message 512 includes identifying information for the particular person, and includes the newly created MII such that the MDM datasets 504 can retain the MII as an enterprise-level cross-reference for the particular person. However, the framework 502 performs no changes to the existing data included in the MDM datasets 504. Thus, the framework 502 has created, stored, and shared a high-level cross-reference for the particular person, for use in the enterprise computing environment 500, without modifying contents of any of the MDM datasets 504 and therefore without compromising the data integrity of any of the MDM datasets 504.

FIG. 5 represents one embodiment of a workflow that is executed using the framework 502 in an enterprise computing environment 500. As described previously with regard to FIG. 4, the workflow is determined by the framework 502 based on alignment of the workflow with the input data message 510. Further, the routing slip is created based on the applicable workflow, or in other words, the routing slip is created to include a plurality of services called to execute the workflow steps, and a sequence or order for the plurality of services. The framework 502 executes each service, in sequence, to generate an MII as a cross-reference for all records associated with a particular person in the enterprise computing environment 500.

Figure 6:
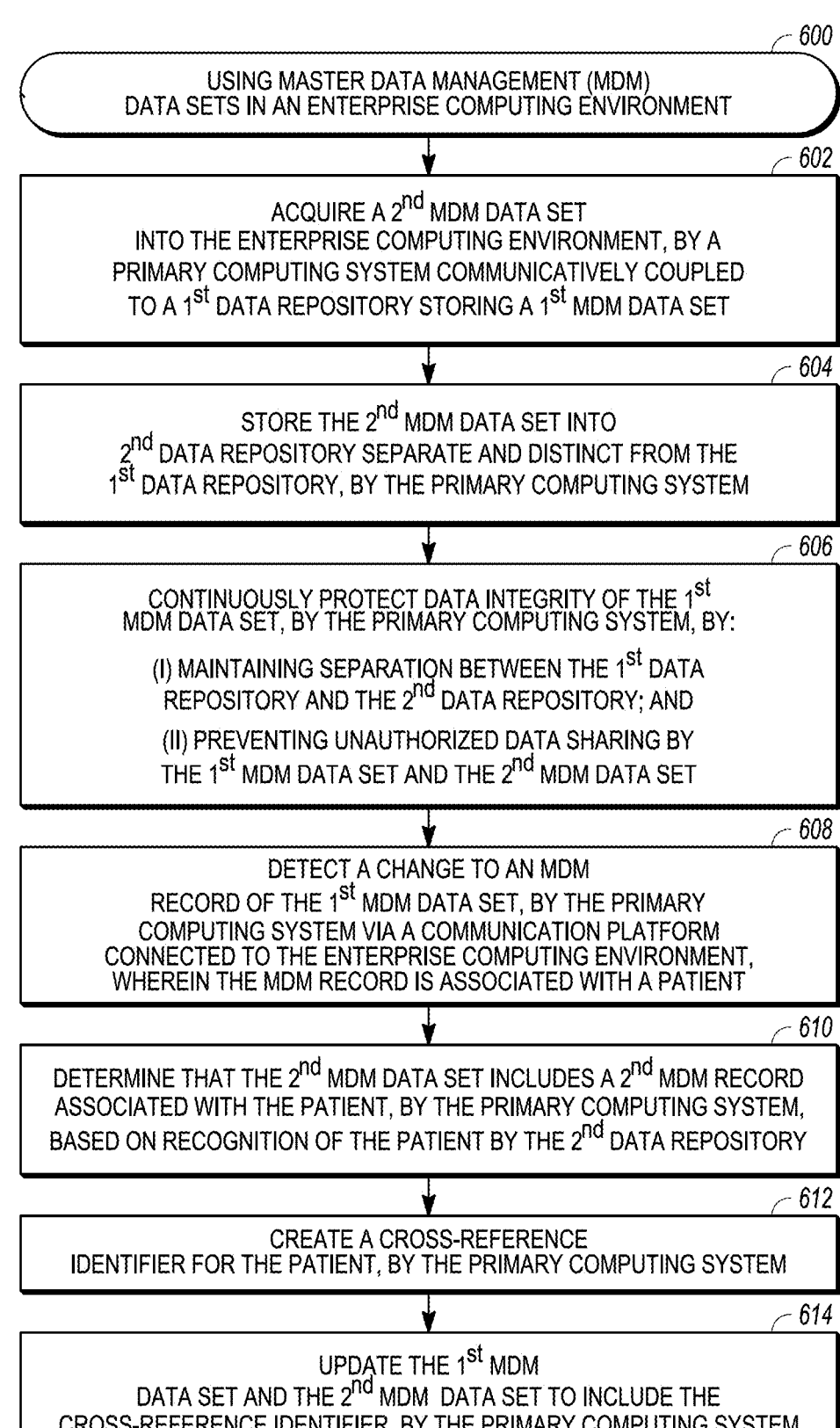
FIG. 6 is a flow chart that illustrates an embodiment of a process for using Master Data Management (MDM) data sets in an enterprise computing environment, in accordance with the disclosed embodiments.

FIG. 6 is a flow chart that illustrates an embodiment of a process 600 for using Master Data Management (MDM) data sets in an enterprise computing environment, in accordance with the disclosed embodiments.

The process 600 acquires a second Master Data Management (MDM) data set into the enterprise computing environment, by a primary computing system communicatively coupled to a first data repository storing a first MDM data set (step 602). Here, the process 600 acquires an MDM data set that is separate and distinct from any existing MDM data sets associated with the enterprise computing environment.

The process 600 stores the second MDM data set into a second data repository separate and distinct from the first data repository, by the primary computing system (step 604), for purposes of maintaining data integrity and/or compliance standards.

The process 600 continuously protecting data integrity of the first MDM data set and the second MDM data set, by the primary computing system (step 606). The process 600 protects data integrity by: (i) maintaining separation between the first data repository and the second data repository, and (ii) preventing unauthorized data sharing by the first MDM data set and the second MDM data set.

The process 600 may maintain separation between the first data repository and the second data repository, by: storing the second MDM data set into a disparate data repository consisting of computing components isolated from the first data repository, by the primary computing system, wherein the second data repository comprises the disparate data repository. One particular embodiment of preventing unauthorized data sharing by the first MDM data set and the second MDM data set is described below with regard to FIG. 7, including additional detail.

The process 600 detects a change to an MDM record of the first MDM data set, by the primary computing system via a communication platform connected to the enterprise computing environment including at least the primary computing system, the first data repository, and the second data repository, wherein the MDM record is associated with a patient (step 608). In some embodiments, the process 600 detects the change to the MDM record, by accessing a data broadcast from the first data repository, via the communication platform, wherein the data broadcast indicates the change to the MDM record.

The process 600 determines that the second MDM data set includes a second MDM record associated with the patient, by the primary computing system, based on recognition of the patient by the second data repository (step 610). In some embodiments, the process 600 detects recognition of the patient by the second data repository, by accessing a data broadcast from the second data repository, via the communication platform, wherein the data broadcast indicates that the second MDM data set includes the second MDM record associated with the patient.

The process 600 creates a cross-reference identifier for the patient, by the primary computing system (step 612). The cross-reference identifier is used as a Master Individual Identifier (MII), or in other words, a high-level identifier associated with the particular patient across MDMs, enabling the enterprise computing environment to use a plurality of separate and distinct MDM data sets without combining the MDM data sets or compromising existing data integrity of the MDM data sets.

The process 600 updates the first MDM data set and the second MDM data set to include the cross-reference identifier, by the primary computing system (step 614). One particular embodiment of step 614 may be performed by process 800 of FIG. 8, which is described below including additional detail. Here, the process 600 associates and stores the MII for use at a high-level, without compromising the data integrity of the MDM data sets.

Figure 7:
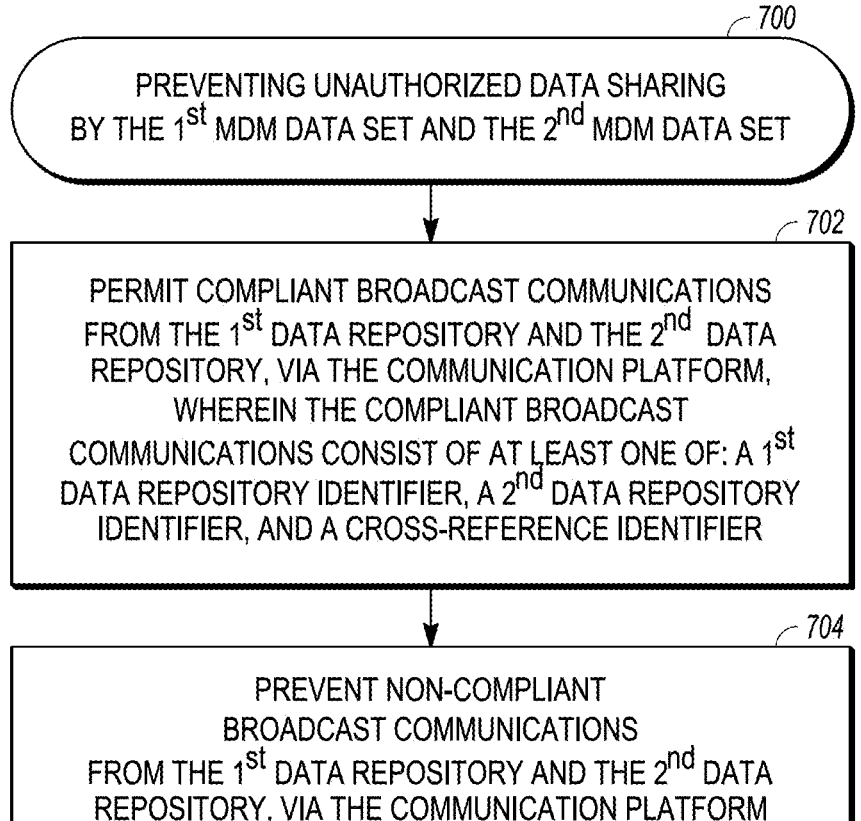
FIG. 7 is a flow chart that illustrates an embodiment of a process for preventing unauthorized data sharing by Master Data Management (MDM) data sets, in accordance with the disclosed embodiments.

FIG. 7 is a flow chart that illustrates an embodiment of a process 700 for preventing unauthorized data sharing by Master Data Management (MDM) data sets, in accordance with the disclosed embodiments. FIG. 7 illustrates one particular embodiment of step 606 of FIG. 6, including additional detail.

The process 700 permits compliant broadcast communications from the first data repository and the second data repository, by the primary computing system via the communication platform, wherein the compliant broadcast communications consist of at least one of: a first data repository identifier, a second data repository identifier, and a cross-reference identifier (step 702).

The process 700 prevents non-compliant broadcast communications from the first data repository and the second data repository, by the primary computing system via the communication platform (step 704).

Figure 8:
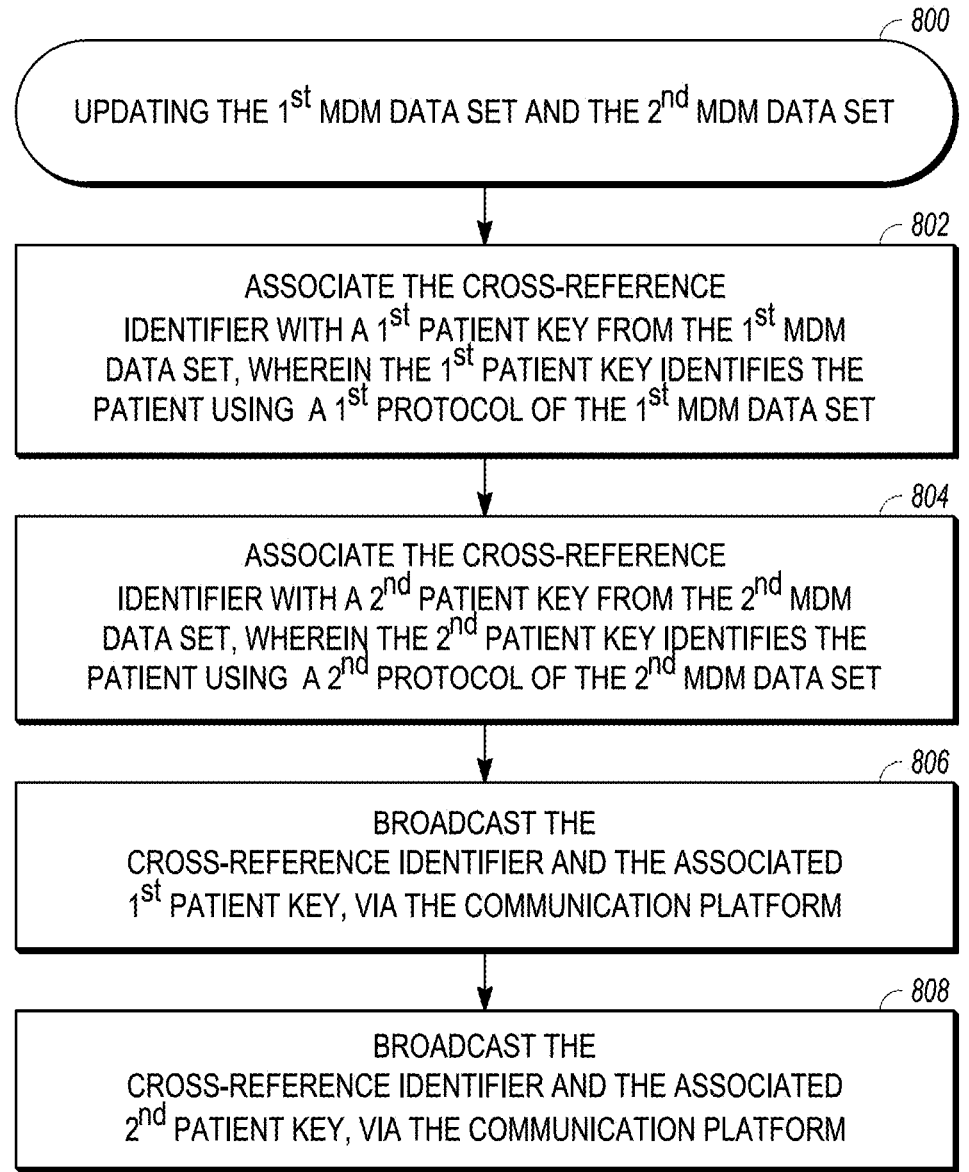
FIG. 8 is a flow chart that illustrates an embodiment of a process for updating Master Data Management (MDM) data sets, in accordance with the disclosed embodiments.

FIG. 8 is a flow chart that illustrates an embodiment of a process 800 for updating Master Data Management (MDM) data sets, in accordance with the disclosed embodiments. FIG. 8 illustrates one particular embodiment of step 614 of FIG. 6, including additional detail.

The process 800 associating the cross-reference identifier with a first patient key from the first MDM data set, to create an associated first patient key, by the primary computing system, wherein the first patient key identifies the patient using a first protocol of the first MDM data set (step 802).

The process 800 associates the cross-reference identifier with a second patient key from the second MDM data set, to create an associated second patient key, by the primary computing system, wherein the second patient key identifies the patient using a second protocol of the second MDM data set (step 804).

The process 800 then updates the first MDM data set and the second MDM data set, by broadcasting the cross-reference identifier via the communication platform, wherein the first data repository and the second data repository are configured to perform event-based records updating in response to an update trigger, and wherein the update trigger includes broadcasting the cross-reference identifier. Here, the process 800 broadcasts the cross-reference identifier and the associated first patient key, by the primary computing system (step 806). The process 800 broadcasts the cross-reference identifier and the associated second patient key, by the primary computing system (step 808).

Figure 9:
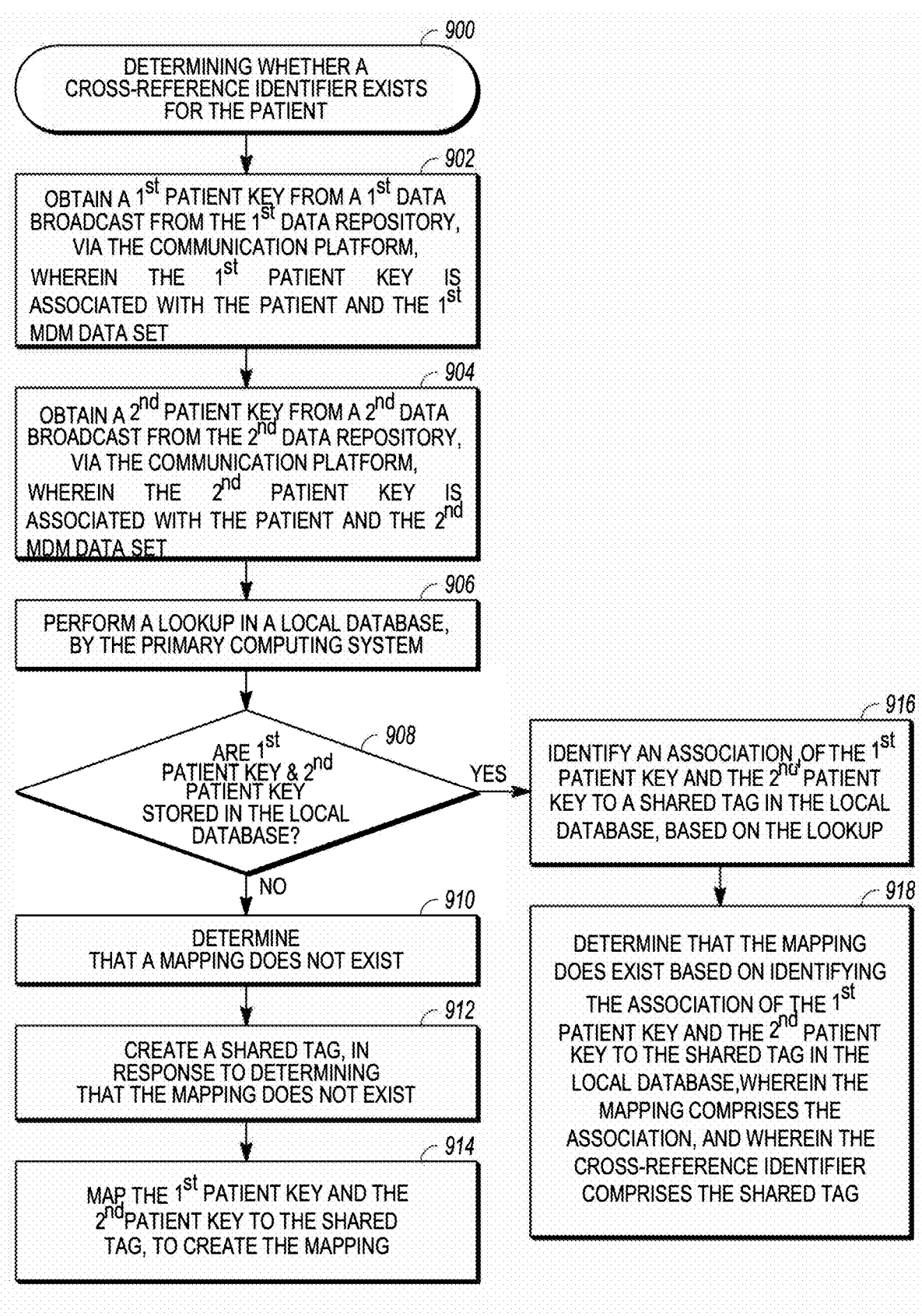
FIG. 9 is a flow chart that illustrates an embodiment of a process for determining whether a cross-reference identifier exists for a patient, in accordance with the disclosed embodiments.

FIG. 9 is a flow chart that illustrates an embodiment of a process 900 for determining whether a cross-reference identifier exists for a patient, in accordance with the disclosed embodiments.

The process 900 obtains a first patient key from a first data broadcast from the first data repository, by the primary computing system via the communication platform, wherein the first patient key is associated with the patient and the first MDM data set (step 902).

The process 900 obtains a second patient key from a second data broadcast from the second data repository, by the primary computing system via the communication platform, wherein the second patient key is associated with the patient and the second MDM data set (step 904).

The process 900 performs a lookup in the local database, by the primary computing system (step 906).

The process 900 determines whether the first patient key and the second patient key are stored in the local database (decision 908). In other words, the process 900 determines whether a mapping to the cross-reference identifier exists for the patient.

When the process 900 determines that the first patient key and the second patient key are stored in the local database (the "Yes" branch of 908), the process 900 identifies existence of an association of the first patient key and the second patient key to a shared tag in the local database, based on the lookup (step 916). Here, the process 900 identifies the mapping of the first patient key and the second patient key to the serialized shared tag in the local database, based on the lookup.

The process 900 then determines that the mapping does exist, by the primary computing system, based on identifying the mapping (step 918). In some embodiments, the process 900 identifies the mapping by identifying the association of the first patient key and the second patient key to the shared tag in the local database, wherein the mapping comprises the association, and wherein the cross-reference identifier comprises the shared tag.

When the process 900 determines that the first patient key and the second patient key are not stored in the local database (the "No" branch of 908), then the process 900 determines that the mapping does not exist, by the primary computing system (step 910).

The process 900 then creates the shared tag, by the primary computing system, wherein the cross-reference identifier comprises the shared tag (step 912). Exemplary embodiments of a shared tag include a Master Individual Identifier (MII). The process 900 maps the first patient key and the second patient key to the shared tag, by the primary computing system, to create the mapping (step 914). Here, the process 900 creates the mapping such that the system using the enterprise computing environment is operable to reference a particular patient across separate and distinct MDM data sets without compromising data integrity of the MDM data sets.

The various tasks performed in connection with processes 600-900 may be performed by software, hardware, firmware, or any combination thereof. For illustrative purposes, the preceding descriptions of processes 600-900 may refer to elements mentioned above in connection with FIGS. 1-5. In practice, portions of processes 600-900 may be performed by different elements of the described system. It should be appreciated that processes 600-900 may include any number of additional or alternative tasks, the tasks shown in FIGS. 6-9 need not be performed in the illustrated order, and one or more of processes 600-900 may be incorporated into a more comprehensive procedure or process having additional functionality not described in detail herein. Moreover, one or more of the tasks shown in FIGS. 6-9 could be omitted from embodiments of the processes 600-900 as long as the intended overall functionality remains intact.

In various embodiments described herein, anyone of the local MDM can start a record for an individual and upon discovery that a record for the same individual is created or exists in a second local MDM, a cross reference (XREF) is created to link the multiple records together and allow access to the separate records directed to a same individual. In an example, the XREF is stored at an enterprise level above the actual records at the local MDM. The check for an existing record for an individual (e.g., does an XREF exist) and the creation of new XREF are event driven. In an example, the event is either the creation of a new record, or a modification of an existing record that does not have an existing XREF. For example during enrollment of an individual into a new plan (e.g., a healthcare plan after changing to a new healthcare plan), there exists records for that individual, such records can be in a different server. The present server (local MDM) triggers a check for an XREF. As the individual has existing records, e.g., at different servers (different local MDM), an XREF exists. The XREF is then assigned to the new record. The XREF check and return can be conducted through an API call.

The computer system that can implement the presently described methods and functions can include memory configured to store computer-executable instructions and records including individual profiles, medical records, plan records, financial records, and the like. Each record can have multiple fields, which may not have a standardized format. The system also includes at least one processor configured to execute the instructions. The instructions include searching for a universal identifier (e.g., XREF) from an enterprise level server (e.g., a MII server). The instructions can further create a new universal identifier (e.g., XREF) if one is not found. The universal identifier can be created by the enterprise level server (e.g., a MII server). The enterprise level server (e.g., a MII server) can store the universal identifier as an entry record in blockchain. The blockchain includes receiving data from the local MDM for the individual and then generating, by a blockchain secret universal individual key ledger, a secret individual key to identify the individual across the enterprise. The secret individual key entry acts an the XREF. The blockchain can be stored across multiple ledgers on multiple servers that are identified by the enterprise level server as having access to the blockchain.

The present disclosure includes embodiments a central authority to issue a central, universal identifier that associates different records to a specific individual. The universal identifier (e.g., XREF) can be a distinct URI or "unique ID". The asset uniquely identifies the individual to the issuing entity system and to other systems in communication with the central authority. Select data about the individual obtained by one or more entities is stored in the central authority or in a network of computerized devices in communication therewith each other or with the central authority, which allows for this data to be queried by all the entities with increased efficiency by tying records together for an individual. In an example, the universal identifier is serialized across all of the local servers (MDM) that will receive or process data related to the individual. In this example, all of the universal identifiers can be stored in the local MDM servers, e.g., within an identifier table. Further improved healthcare experience can be provided by identifying all of the records associated with a specific individual directly across multiple record stores by more quickly identifying the individual's records during an identity-related interaction (for example, an identity verification, a receipt of a benefit, or other suitable identity-related interaction) with other MDM servers in communication directly with other MDM servers.

In an example, the first health records and second health records include identifying a unique member identifier corresponding to the first member (e.g., XREF) and scanning the received streaming data for data values including the member identifier. The instructions further include routing the data values including the member identifier to the appropriate local MDM, while tagging the incoming data with the unique member identifier. The present system can have multiple local MDMs processing member data in parallel. For example, the multiple local MDMS can be processing nodes for processing data values in parallel. The local MDMs can route the data values to be tagged with the unique identifier or hold the data until the data is tagged with an existing unique identifier or a newly created unique identifier. In an example, the data records remain an the local MDM level and the unique identifier for an individual is created at the enterprise level (MII level). While the unique identifier is created and the master record of unique identifiers are stored at the enterprise level (e.g., MII), the actual data records remain distributed at the MDM level. In an example embodiment, each data record at the local MDM level must be tagged with a unique identifier. At the enterprise level there is a one-to-one relationship between the member and unique identifier linked to the member, but the unique identifier can be tagged to multiple records associated with the member at the local MDM level, within a single MDM server or across multiple MDM servers.

In an example the unique identifier is a hash value of various data values unique to the individual, e.g., a member of an insurance plan or health plan.

Techniques and technologies may be described herein in terms of functional and/or logical block components, and with reference to symbolic representations of operations, processing tasks, and functions that may be performed by various computing components or devices. Such operations, tasks, and functions are sometimes referred to as being computer-executed, computerized, software-implemented, or computer-implemented. In practice, one or more processor devices can carry out the described operations, tasks, and functions by manipulating electrical signals representing data bits at memory locations in the system memory, as well as other processing of signals. The memory locations where data bits are maintained are physical locations that have particular electrical, magnetic, optical, or organic properties corresponding to the data bits. It should be appreciated that the various block components shown in the figures may be realized by any number of hardware, software, and/or firmware components configured to perform the specified functions. For example, an embodiment of a system or a component may employ various integrated circuit components, e.g., memory elements, digital signal processing elements, logic elements, look-up tables, or the like, which may carry out a variety of functions under the control of one or more microprocessors or other control devices.

When implemented in software or firmware, various elements of the systems described herein are essentially the code segments or instructions that perform the various tasks. The program or code segments can be stored in a processor-readable medium or transmitted by a computer data signal embodied in a carrier wave over a transmission medium or communication path. The "computer-readable medium", "processor-readable medium", or "machine-readable medium" may include any medium that can store or transfer information. Examples of the processor-readable medium include an electronic circuit, a semiconductor memory device, a ROM, a flash memory, an erasable ROM (EROM), a floppy diskette, a CD-ROM, an optical disk, a hard disk, a fiber optic medium, a radio frequency (RF) link, or the like. The computer data signal may include any signal that can propagate over a transmission medium such as electronic network channels, optical fibers, air, electromagnetic paths, or RF links. The code segments may be downloaded via computer networks such as the Internet, an intranet, a LAN, or the like.

The preceding description refers to elements or nodes or features being "connected" or "coupled" together. As used herein, unless expressly stated otherwise, "coupled" means that one element/node/feature is directly or indirectly joined to (or directly or indirectly communicates with) another element/node/feature, and not necessarily mechanically, e.g., electrically or in communication connection. Likewise, unless expressly stated otherwise, "connected" means that one element/node/feature is directly joined to (or directly communicates with) another element/node/feature, and not necessarily mechanically. Thus, although the schematics shown in FIGS. 1-5 depict exemplary arrangements of elements, additional intervening elements, devices, features, or components may be present in an embodiment of the depicted subject matter.

In addition, certain terminology may also be used in the preceding description for the purpose of reference only, and thus are not intended to be limiting. For example, terms such as "upper", "lower", "above", and "below" refer to directions in the drawings to which reference is made. Terms such as "front", "back", "rear", "side", "outboard", and "inboard" describe the orientation and/or location of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second", and other such numerical terms referring to structures do not imply a sequence or order unless clearly indicated by the context.

For the sake of brevity, conventional techniques related to signal processing, data transmission, signaling, network control, and other functional aspects of the systems (and the individual operating components of the systems) may not be described in detail herein. Furthermore, the connecting lines shown in the various figures contained herein are intended to represent exemplary functional relationships and/or physical couplings between the various elements. It should be noted that many alternative or additional functional relationships or physical connections may be present in an embodiment of the subject matter.

For purposes of the present disclosure, embodiments described herein may include additional components, elements, or features that cooperate to support the desired functionality. Such additional components, elements, or features may include duplicates. Thus, as described herein, "a" component, "an" element or "a" feature may indicate one, or more than one, of the component, element, or feature.

Some of the functional units described in this specification have been referred to as "modules" in order to more particularly emphasize their implementation independence. For example, functionality referred to herein as a module may be implemented wholly, or partially, as a hardware circuit comprising custom VLSI circuits or gate arrays, off-the-shelf semiconductors such as logic chips, transistors, or other discrete components. A module may also be implemented in programmable hardware devices such as field programmable gate arrays, programmable array logic, programmable logic devices, or the like. Modules may also be implemented in software for execution by various types of processors. An identified module of executable code may, for instance, comprise one or more physical or logical modules of computer instructions that may, for instance, be organized as an object, procedure, or function. Nevertheless, the executables of an identified module need not be physically located together, but may comprise disparate instructions stored in different locations that, when joined logically together, comprise the module and achieve the stated purpose for the module. Indeed, a module of executable code may be a single instruction, or many instructions, and may even be distributed over several different code segments, among different programs, and across several memory devices. Similarly, operational data may be embodied in any suitable form and organized within any suitable type of data structure. The operational data may be collected as a single data set, or may be distributed over different locations including over different storage devices, and may exist, at least partially, merely as electronic signals on a system or network.

While at least one exemplary embodiment has been presented in the foregoing detailed description, it should be appreciated that a vast number of variations exist. It should also be appreciated that the exemplary embodiment or embodiments described herein are not intended to limit the scope, applicability, or configuration of the claimed subject matter in any way. Rather, the foregoing detailed description will provide those skilled in the art with a convenient road map for implementing the described embodiment or embodiments. It should be understood that various changes can be made in the function and arrangement of elements without departing from the scope defined by the claims, which includes known equivalents and foreseeable equivalents at the time of filing this patent application.

What is claimed is:

1. A system for managing Master Data Management (MDM) data sets in an enterprise computing environment, the system comprising:

a first data repository comprising at least a first processing element, a memory element, and a first communication element, wherein the first data repository is configured to store and maintain a first Master Data Management (MDM) data set;

a communication platform comprising a broadcast communication medium connecting a primary computing system to at least the first data repository in the enterprise computing environment; and the primary computing system comprising at least one processor and a system memory element, wherein the primary computing system is communicatively coupled to the first data repository using the communication platform, and wherein the primary computing system is configured to:

acquire a second Master Data Management (MDM) data set into the enterprise computing environment;

store the second MDM data set into a second data repository separate and distinct from the first data repository;

continuously protect data integrity of the first MDM data set and the second MDM data set, by: (i) maintaining separation between the first data repository and the second data repository, and (ii) preventing unauthorized data sharing by the first MDM data set and the second MDM data set;

detect a change to an MDM record of the first MDM data set, via the communication platform connected to the enterprise computing environment including at least the primary computing system, the first data repository, and the second data repository, wherein the MDM record is associated with a patient;

determine that the second MDM data set includes a second MDM record associated with the patient, based on recognition of the patient by the second data repository;

create a cross-reference identifier for the patient; and update the first MDM data set and the second MDM data set to include the cross-reference identifier, via the communication platform.

2. The system of claim 1, wherein the primary computing system is further configured to maintain separation between the first data repository and the second data repository, by:

storing the second MDM data set into a disparate data repository consisting of computing components isolated from the first data repository, by the primary computing system, wherein the second data repository comprises the disparate data repository.

3. The system of claim 1, wherein the primary computing system is further configured to prevent unauthorized data sharing by the first MDM data set and the second MDM data set, by:

permitting compliant broadcast communications from the first data repository and the second data repository, via the communication platform, wherein the compliant broadcast communications consist of at least one of: a first data repository identifier, a second data repository identifier, and a cross-reference identifier; and preventing non-compliant broadcast communications from the first data repository and the second data repository, via the communication platform.

4. The system of claim 1, wherein the primary computing system is further configured to detect the change to the MDM record, by:

accessing a data broadcast from the first data repository, via the communication platform, wherein the data broadcast indicates the change to the MDM record.

5. The system of claim 1, wherein the primary computing system is further configured to detect recognition of the patient by the second data repository, by:

accessing a data broadcast from the second data repository, via the communication platform, wherein the data broadcast indicates that the second MDM data set includes the second MDM record associated with the patient.

6. The system of claim 1, wherein the primary computing system is further configured to update the first MDM data set and the second MDM data set, by:

broadcasting the cross-reference identifier via the communication platform, wherein the first data repository and the second data repository are configured to perform event-based records updating in response to an update trigger, and wherein the update trigger includes broadcasting the cross-reference identifier.

7. The system of claim 1, wherein the primary computing system is further configured to update the first MDM data set and the second MDM data set, by:

associating the cross-reference identifier with a first patient key from the first MDM data set, to create an associated first patient key, by the primary computing system, wherein the first patient key identifies the patient using a first protocol of the first MDM data set;

associating the cross-reference identifier with a second patient key from the second MDM data set, to create an associated second patient key, by the primary computing system, wherein the second patient key identifies the patient using a second protocol of the second MDM data set;

broadcasting the cross-reference identifier and the associated first patient key, via the communication platform; and broadcasting the cross-reference identifier and the associated second patient key, via the communication platform.

8. The system of claim 1, wherein the primary computing system is further configured to:

determine whether a mapping to the cross-reference identifier exists for the patient; and when the mapping does not exist, create the cross-reference identifier.

9. The system of claim 8, wherein the primary computing system is further configured to:

obtain a first patient key from a first data broadcast from the first data repository, via the communication platform, wherein the first patient key is associated with the patient and the first MDM data set;

obtain a second patient key from a second data broadcast from the second data repository, via the communication platform, wherein the second patient key is associated with the patient and the second MDM data set;

determine whether the first patient key and the second patient key are mapped to a shared tag; and when the first patient key and the second patient key are not mapped to a shared tag, determine that the mapping does not exist;

create the shared tag, wherein the cross-reference identifier comprises the shared tag; and map the first patient key and the second patient key to the shared tag, to create the mapping.

10. The system of claim 9, wherein the primary computing system is further configured to:

serialize the shared tag, to create a serialized shared tag;

store the mapping including the serialized shared tag in a local database;

determine whether the first patient key and the second patient key are mapped to the shared tag, by:

performing a lookup in the local database; and identifying the mapping of the first patient key and second patient key to the serialized shared tag in the local database, based on the lookup; and determining that the mapping does exist, based on identifying the mapping in the local database.

11. A method for managing Master Data Management (MDM) data sets in an enterprise computing environment, the method comprising:

acquiring a second Master Data Management (MDM) data set into the enterprise computing environment, by a primary computing system communicatively coupled to a first data repository storing a first MDM data set;

storing the second MDM data set into a second data repository separate and distinct from the first data repository, by the primary computing system;

continuously protecting data integrity of the first MDM data set and the second MDM data set, by the primary computing system, by: (i) maintaining separation between the first data repository and the second data repository, and (ii) preventing unauthorized data sharing by the first MDM data set and the second MDM data set;

detecting a change to an MDM record of the first MDM data set, by the primary computing system via a communication platform connected to the enterprise computing environment including at least the primary computing system, the first data repository, and the second data repository, wherein the MDM record is associated with a patient;

determining that the second MDM data set includes a second MDM record associated with the patient, by the primary computing system, based on recognition of the patient by the second data repository;

creating a cross-reference identifier for the patient, by the primary computing system; and updating the first MDM data set and the second MDM data set to include the cross-reference identifier, by the primary computing system.

12. The method of claim 11, wherein maintaining the separation between the first data repository and the second data repository, further comprises:

storing the second MDM data set into a disparate data repository consisting of computing components isolated from the first data repository, by the primary computing system, wherein the second data repository comprises the disparate data repository.

13. The method of claim 11, wherein preventing unauthorized data sharing by the first MDM data set and the second MDM data set, further comprises:

permitting compliant broadcast communications from the first data repository and the second data repository, by the primary computing system via the communication platform, wherein the compliant broadcast communications consist of at least one of: a first data repository identifier, a second data repository identifier, and a cross-reference identifier; and preventing non-compliant broadcast communications from the first data repository and the second data repository, by the primary computing system via the communication platform.

14. The method of claim 11, wherein detecting the change to the MDM record further comprises:

accessing a data broadcast from the first data repository, by the primary computing system via the communication platform, wherein the data broadcast indicates the change to the MDM record.

15. The method of claim 11, wherein detecting recognition of the patient by the second data repository, further comprises:

accessing a data broadcast from the second data repository, by the primary computing system via the communication platform, wherein the data broadcast indicates that the second MDM data set includes the second MDM record associated with the patient.

16. The method of claim 11, wherein updating the first MDM data set and the second MDM data set, further comprises:

broadcasting the cross-reference identifier via the communication platform, by the primary computing system, wherein the first data repository and the second data repository are configured to perform event-based records updating in response to an update trigger, and wherein the update trigger includes broadcasting the cross-reference identifier.

17. The method of claim 11, wherein updating the first MDM data set and the second MDM data set, further comprises:

associating the cross-reference identifier with a first patient key from the first MDM data set, to create an associated first patient key, by the primary computing system, wherein the first patient key identifies the patient using a first protocol of the first MDM data set;

associating the cross-reference identifier with a second patient key from the second MDM data set, to create an associated second patient key, by the primary computing system, wherein the second patient key identifies the patient using a second protocol of the second MDM data set;

broadcasting the cross-reference identifier and the associated first patient key, by the primary computing system; and broadcasting the cross-reference identifier and the associated second patient key, by the primary computing system.

18. The method of claim 11, further comprising:

obtaining a first patient key from a first data broadcast from the first data repository, by the primary computing system via the communication platform, wherein the first patient key is associated with the patient and the first MDM data set;

obtaining a second patient key from a second data broadcast from the second data repository, by the primary computing system via the communication platform, wherein the second patient key is associated with the patient and the second MDM data set;

determining whether the first patient key and the second patient key are mapped to a shared tag; and when the first patient key and the second patient key are not mapped to a shared tag, determining that the mapping does not exist, by the primary computing system;

creating the shared tag, by the primary computing system, wherein the cross-reference identifier comprises the shared tag; and mapping the first patient key and the second patient key to the shared tag, by the primary computing system, to create the mapping.

19. The method of claim 18, further comprising:

serializing the shared tag, by the primary computing system, to create a serialized shared tag;

storing the mapping including the serialized shared tag in a local database, by the primary computing system;

wherein determining whether the first patient key and the second patient key are mapped to the shared tag, further comprises:

performing a lookup in the local database, by the primary computing system;

identifying the mapping of the first patient key and the second patient key to the serialized shared tag in the local database, based on the lookup; and determining that the mapping does exist, by the primary computing system, based on identifying the mapping.

* * * * *